(12) United States Patent
Tominaga

(10) Patent No.: US 6,459,759 B1
(45) Date of Patent: Oct. 1, 2002

(54) X-RAY TOMOGRAPHY APPARATUS AND METHOD OF TAKING TOMOGRAPHIC IMAGE OF OBJECT WITH THE APPARATUS

(75) Inventor: Tamotsu Tominaga, Akishima (JP)

(73) Assignee: Hitachi Denshi Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/525,025

(22) Filed: Mar. 14, 2000

(30) Foreign Application Priority Data

Mar. 15, 1999 (JP) .......................................... 11-067866

(51) Int. Cl.$^7$ .............................................. G01N 23/04
(52) U.S. Cl. .......................................... 378/22; 378/24
(58) Field of Search .................................... 378/21–27

(56) References Cited

U.S. PATENT DOCUMENTS 5,351,278 A * 9/1994 Koshishiba et al. .......... 378/22
5,388,136 A * 2/1995 Halliday et al. ............. 378/58

\* cited by examiner

*Primary Examiner*—David P. Porta
(74) *Attorney, Agent, or Firm*—Antonelli, Terry, Stout & Kraus, LLP

(57) ABSTRACT

In an X-ray tomography apparatus and a method of taking tomograms inside an object through the use of the X-ray tomography apparatus, positioning of the object and operation for taking tomograms are carried out in accordance with the following procedures. An X-ray beam is irradiated to the object. An X-ray beam transmitting through the object is detected and a transmission image of the object is generated on the basis of the detected X-ray beam. While watching the transmission image of the object on a display, the object is moved by means of a moving mechanism coupled to a drive unit to change an X-ray irradiation area of the object and the object is stopped at a desired position. The moving mechanism is disconnected from the drive unit. The object irradiated with the X-ray beam is rotated by means of a rotating mechanism about a rotation axis inclined with respect to an irradiation axis of the X-ray beam. An X-ray beam transmitting through the object is detected by means of an X-ray detection unit and a detection image is rotated in synchronism with the rotation of the object. On the basis of a signal representing a rotating image, a tomographic image of the object on a plane including an intersection of the rotation axis and the irradiation axis is generated.

6 Claims, 8 Drawing Sheets

X-RAY TOMOGRAPHY APPARATUS AND METHOD OF TAKING TOMOGRAPHIC IMAGE OF OBJECT WITH THE APPARATUS

BACKGROUND OF THE INVENTION

An x-ray laminography apparatus is a kind of X-ray tomography apparatus for taking tomographic images of an object. The X-ray laminography apparatus has important features, noted below by which it differs from other types of X-ray tomography apparatus. More particularly, in the X-ray laminography apparatus, an X-ray beam is irradiated in a direction which is oblique to an object to be measured, so that the X-ray beam transmitting through the object obliquely thereof is detected by a detection unit. During the tomography, the object and an X-ray detection image are rotated in synchronism with each other on a plane which intersects an X-ray irradiation axis and image processing for adding a plurality of rotation images obtained during the synchronous rotation is carried out, thereby making it possible to selectively obtain only an image on a tomographic plane extending at a specified depth inside of the object. The thus obtained image is a tomogram on the rotation plane including the intersection of the rotation axis of the object and the X-ray irradiation axis. A fundamental measuring method and its principle are described in U.S. Pat. No. 5,351,278 to Koshishiba et al and will not be detailed herein.

For example, the X-ray laminography apparatus is used either to observe only a specified layer inside a multilayer electronic circuit board to find defects or to non-destructively inspect an internal portion at a specified depth of electronic parts, mechanical parts or other matters which cannot be seen from the outside.

FIG. 8 diagrammatically shows the fundamental construction of the X-ray laminography apparatus. As shown in FIG. 8, an object 50 to be measured which is held on a rotary stage 16 having a rotation axis 13 inclined with respect to a radiation direction 4 of an X-ray beam is rotated and an X-ray image detected on a detection surface orthogonal to the rotation axis 13 is rotated: in synchronism with the rotation of the object 50 to belmeasured, so that a tomographic image on a rotary plane where a line 4 connecting an X-ray source 1 and the center of the detection surface intersects the rotation axis 13 can be obtained. Reference numeral 60 designates an xy-stage adapted to move the object 50 on a two-dimensional plane to change an X-ray irradiation area.

In the case of a conventional X-ray laminography apparatus, the xy-stage 60 is movable within a plane on the rotary stage 16 for positioning the object 50 to an observation position. The rotary stage 16 is rotatable endlessly, thus making it difficult to move the xy-stage 60 by driving it with a motor. The reason for this is that the motor and a mechanism for horizontally moving the stage are arranged on the xy-stage 60 and caused to rotate by the rotary stage 16 and so it is very difficult to supply electric power externally and continuously to the motor rotating along with the xy-stage 60. Inevitably, the xy-stage 60 used for moving the object 50 horizontally is moved horizontally so as to change the observation position of the object.

Therefore, when the observation position of the object 50 is desired to be changed, positioning of the object 50 must be carried out by getting the X-ray source turned off temporarily for preventing the operator from encountering radiation. For example, when observing an internal layer of a multilayer printed circuit board or an internal structure of electronic parts or mechanical parts, positioning is conducted without resort to visual reference to any X-ray transmission image and in fact, positioning to an intended observation position cannot be effected accurately within a short period of time.

Conceivably, a method may be proposed in which an xy-stage drive motor is arranged on the rotary stage 16 with the aim of remotely operating the xy-stage and electric power is supplied to the motor through slip rings and brush electrodes which are movable while being in contact to each other. In this proposal, however, disposition of the slip rings and brushes in a Central opening 70 of rotary shaft through which the X-ray beam passes must be avoided and they are required to be disposed at the outer periphery of the rotary shaft, raising problems that the sliding speed of the brushes becomes high to accelerate deterioration of the brushes and the apparatus as a whole becomes large and costly.

The conventional X-ray laminography technology is very excellently featured in that high-resolution tomographic images can be obtained on substantially real time base but nevertheless it has failed to contribute to widespread use of practical apparatus.

SUMMARY OF THE INVENTION

It is an object of the present invention to provide an X-ray tomography apparatus capable of positioning an object to be measured to a desired observation position while permitting an X-ray transmission image of the object for seeking an area of desired tomographic image and an X-ray tomography method using the apparatus.

A second object of the invention is to provide a compact, inexpensive and highly-reliable X-ray tomography apparatus capable of positioning an object to be measured to a desired observation position while permitting an X-ray transmission image of the object to be watched and an X-ray tomography method using the apparatus.

A method of taking tomograms inside an object with an X-ray tomography apparatus according to the present invention comprises the following procedures. More particularly, an X-ray beam is irradiated to the object. An X-ray beam transmitting through the object is detected and a transmission image of the object is generated on the basis of the detected X-ray beam. While watching the transmission image of the object, the object is moved by means of a moving mechanism coupled to a drive unit to change an X-ray irradiation area of the object and the object is stopped at a desired position. The moving mechanism is disconnected from the drive unit. The object being irradiated with the X-ray beam is rotated about a rotation axis which is inclined with respect to an irradiation axis of the X-rays beam. An X-ray beam transmitting through the object is detected, a detected image is rotated in synchronism with the rotation of the object to provide a rotation image, and an image on a tomographic plane in the object which includes an intersection of the rotation and irradiation axes is generated on the basis of the rotation image.

According to the invention, an X-ray tomography apparatus for taking tomograms inside an object comprises an X-ray source for irradiating an X-ray beam to the object, a moving mechanism for moving the object to change an X-ray irradiation area of the object, a rotating mechanism for rotating the object about a rotation axis which is inclined by a predetermined angle with respect to an irradiation axis of the X-ray beam, a control unit for controlling the moving mechanism to cause it to move the object to a designated position so as to change an X-ray irradiation area of the object when the rotating mechanism is stopping at a predetermined position, and an X-ray detection unit for detecting a transmission X-ray beam, rotating a detected image in synchronism with the rotation of the object to provide a rotation image of the object and converting the rotation image into an electric signal.

While observing a transmission image of the object on the monitor screen, an operator can remotely move the object through the medium of the moving mechanism to stop the object at a desired observation position. A tomographic image of the object is taken at the observation position. During a series of operations ranging over positioning of the object and tomography, the operator can perform remote control from a position distant from the tomography apparatus without interrupting irradiation of the X-ray beam and a desired tomogram can be taken accurately within a short period of time.

Besides, according to the invention, an X-ray tomography apparatus for taking tomograms inside an object comprises an X-ray source for irradiating an X-ray beam to the object, a stationary base, first, second and third motors fixed to the stationary base, a hollow shaft driven to rotate by the first motor and having an opening in the center of rotation, an x-stage base fixed to the hollow shaft, x-guide rails fixed on the x-stage base, an x-stage slidable on the guide rails, y-guide rails fixed on the x-stage, a y-stage slidable on the y-guide fails and carrying the object, an angular position sensor for detecting a rotation position of the x-stage base, a first bevel gear mounted to a rotary shaft of the second motor, an x-stage drive unit having a second bevel gear and operative to move the x-stage on the x-guide rails as the second bevel gear rotates, a third bevel gear mounted to a rotary shaft of the third motor, and a y-stage drive unit having a fourth bevel gear and operative to move the y-stage on the y-stage rails as the fourth bevel gear rotates, the y-stage drive unit being supported on the x-stage and the fourth bevel gear being always held at a fixed position on the x-stage regardless of the movement of the x-stage.

The X-ray tomography apparatus according to the invention further comprises a first actuator for moving the first bevel gear to bring it into engagement with the second bevel gear, a second actuator for moving the third bevel gear to bring it into engagement with the fourth bevel gear, a control unit responsive to detection of a predetermined rotation angle by the angular position sensor to stop the rotation of the first motor, control the first and second actuators to release engagement of the first bevel gear with the second bevel gear and bring the third bevel gear into engagement with the fourth bevel gear, and an X-ray detection unit for detecting an X-ray beam transmitting through the object and passing through the opening to provide a detection image, rotating the detection image in synchronism with the rotation of the object to provide a rotation image and generating a tomographic image from the rotation image.

According to the X-ray tomography apparatus according to the invention, since the second and third motors for driving the xy-stage are fixed to the stationary base and electric power can always be supplied externally regardless of movement of the rotary xy-stage without using any slip rings and brushes, the operator can perform remote control from a position distant from the tomography apparatus without interrupting irradiation of the X-ray beam during a series of operations ranging over positioning of the object and tomography and a desired tomogram can be taken accurately within a short period of time. Further, since the y-stage drive unit is supported on the x-stage and the fourth bevel gear for moving the y-stage is always held at a fixed position on the x-stage regardless of slide movement of the x-stage, operation for positioning the object can be effected smoothly. The X-ray tomography apparatus of the invention is not increased in size to have a mechanism capable of remotely controlling the xy-stage.

The present invention is in no way limited to embodiments to be described hereinafter in the present specification. Those skilled in the art can obtain the same effects by using different mechanisms and modification which can fulfil the function comparable to that of elements and mechanisms used in embodiments disclosed in the present specification.

DESCRIPTION OF THE EMBODIMENTS

An embodiment of the present invention will be described hereunder with reference to FIGS. 1–7 and FIGS. 9–10.

Figure 1:
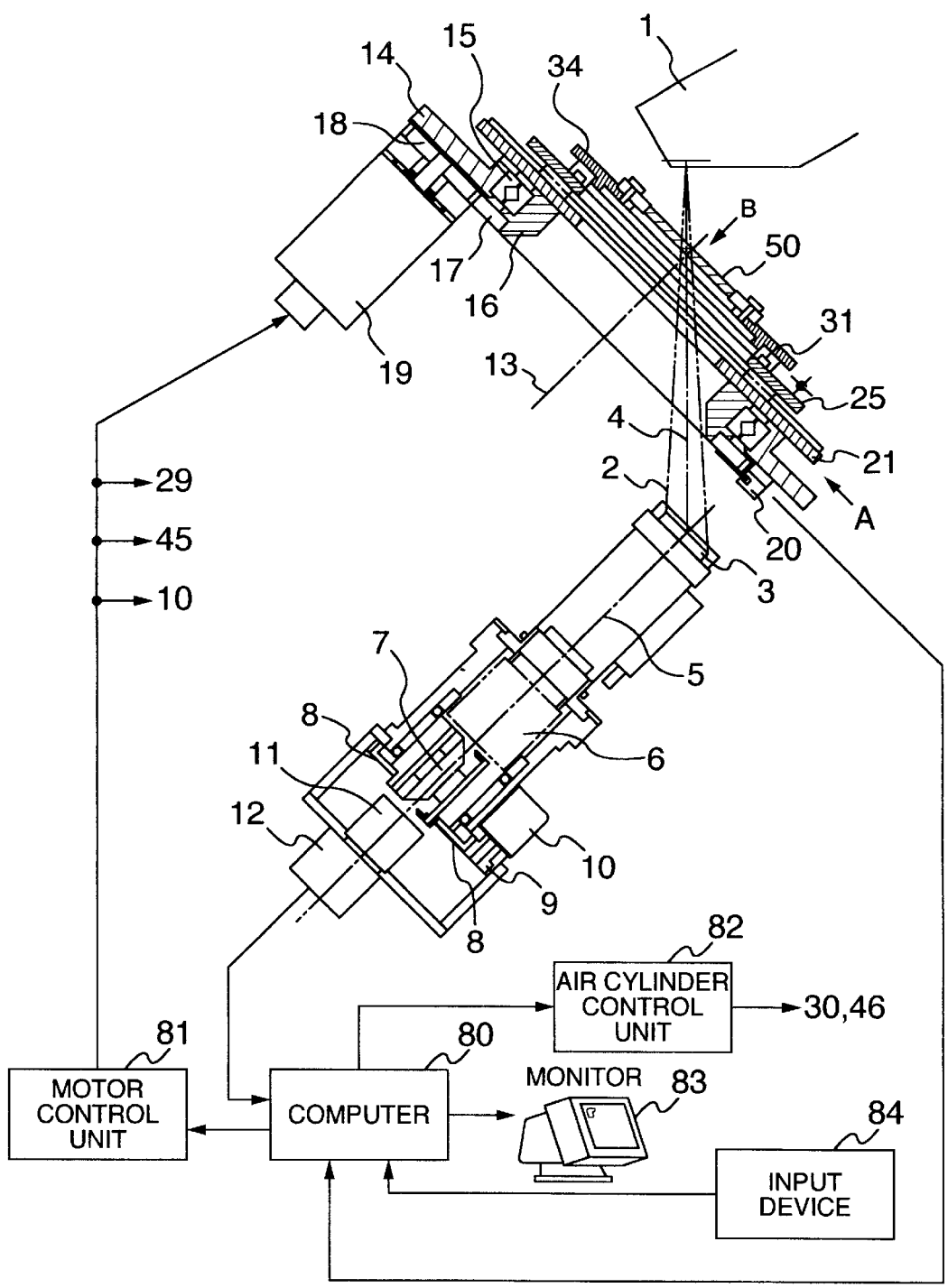
FIG. 1 is a side view, partly sectioned, of an embodiment of an X-ray tomography apparatus according to the invention.
Figure 2:
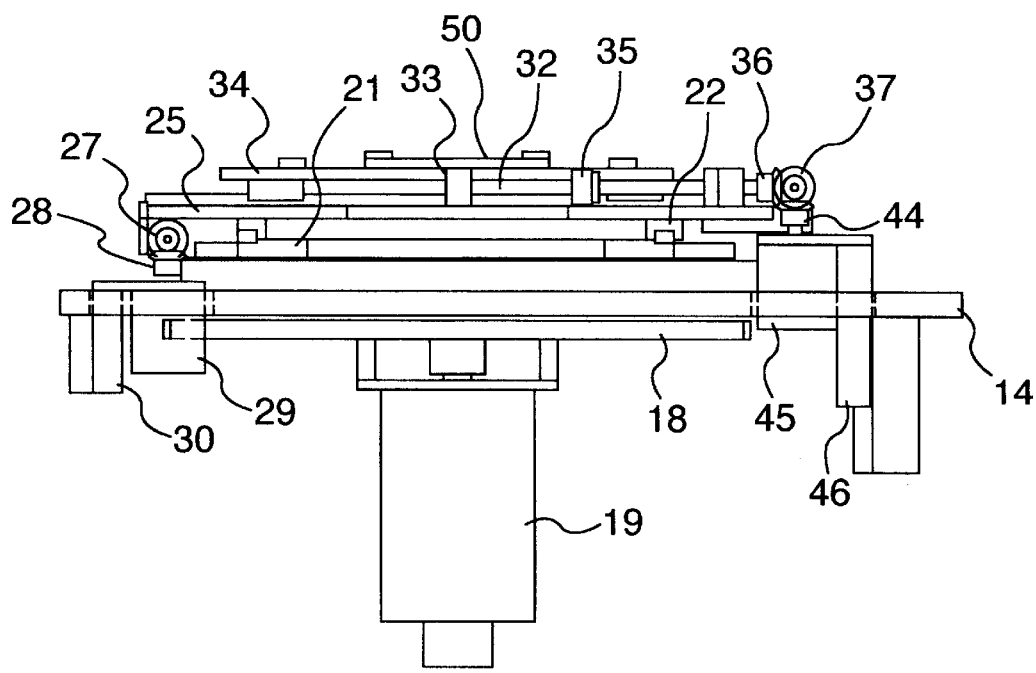
FIG. 2 is a side view of a stage mechanism in the embodiment of the invention.
Figure 3:
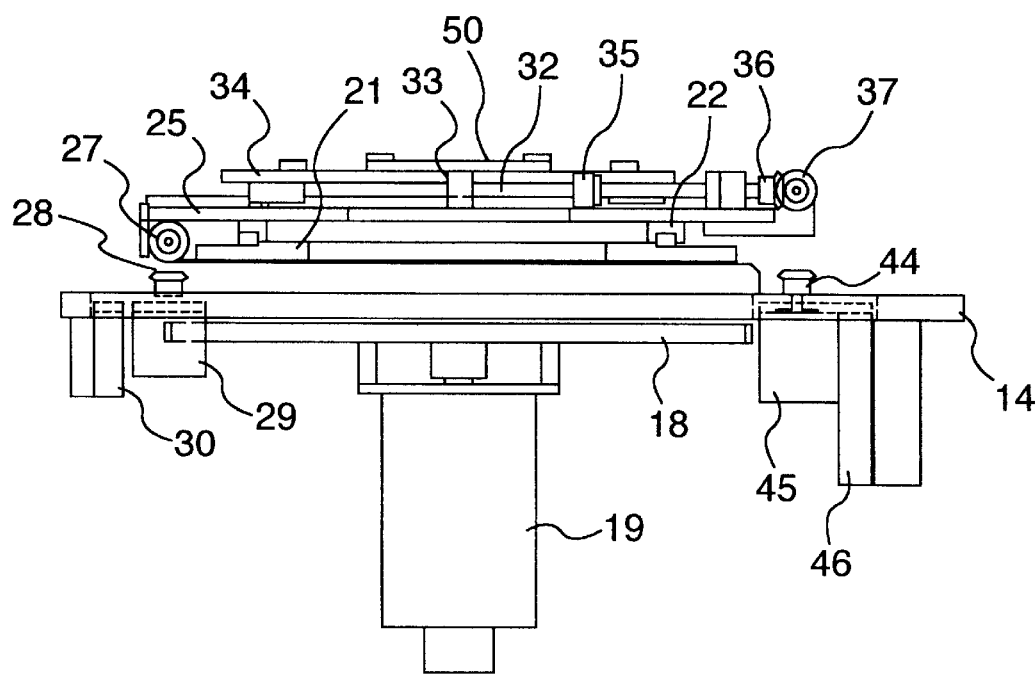
FIG. 3 is a side view showing the stage mechanism in the embodiment when engagement of drive gears is released.
Figure 4:
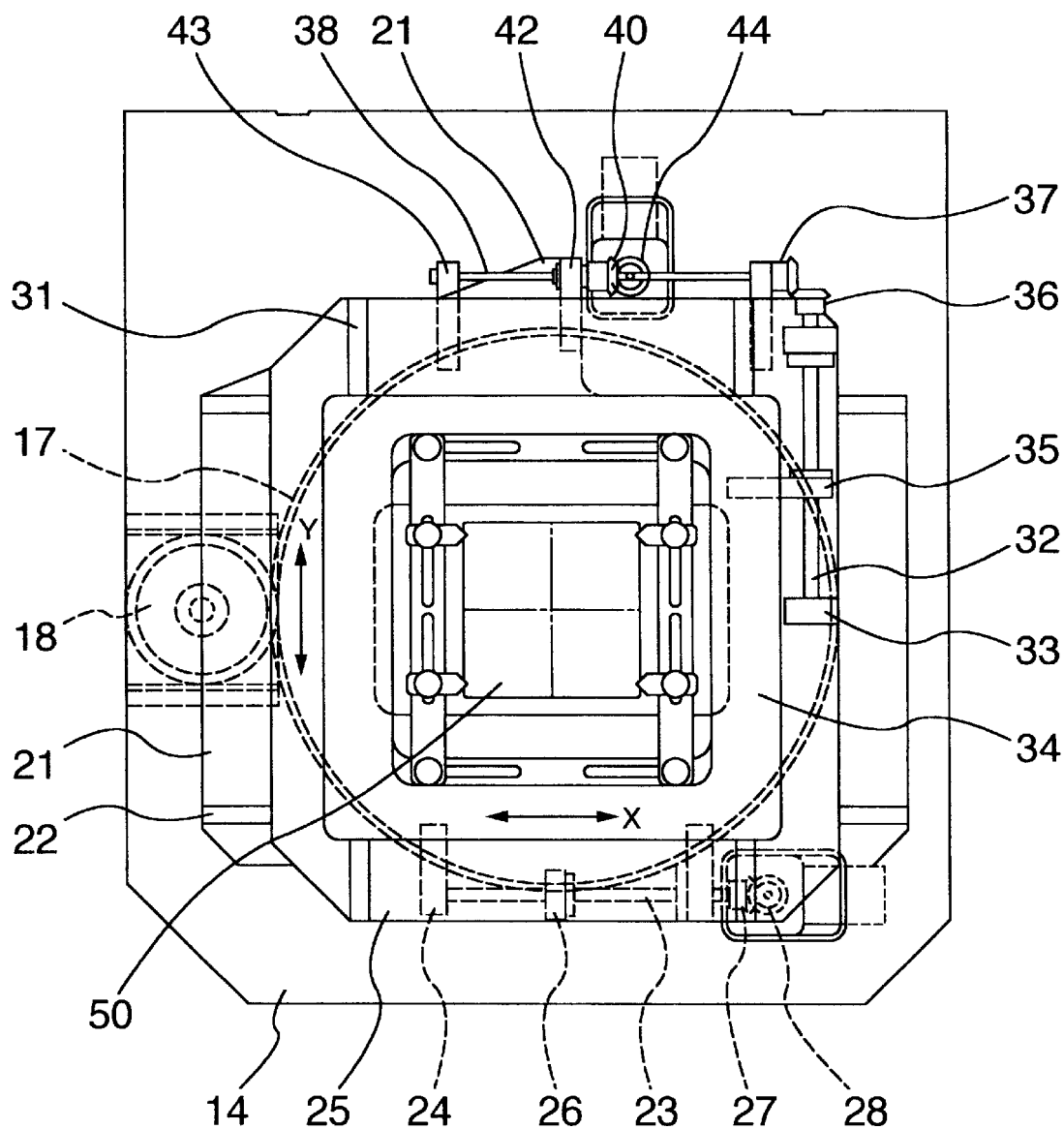
FIG. 4 is a plan view of the stage mechanism in the embodiment.
Figure 5:
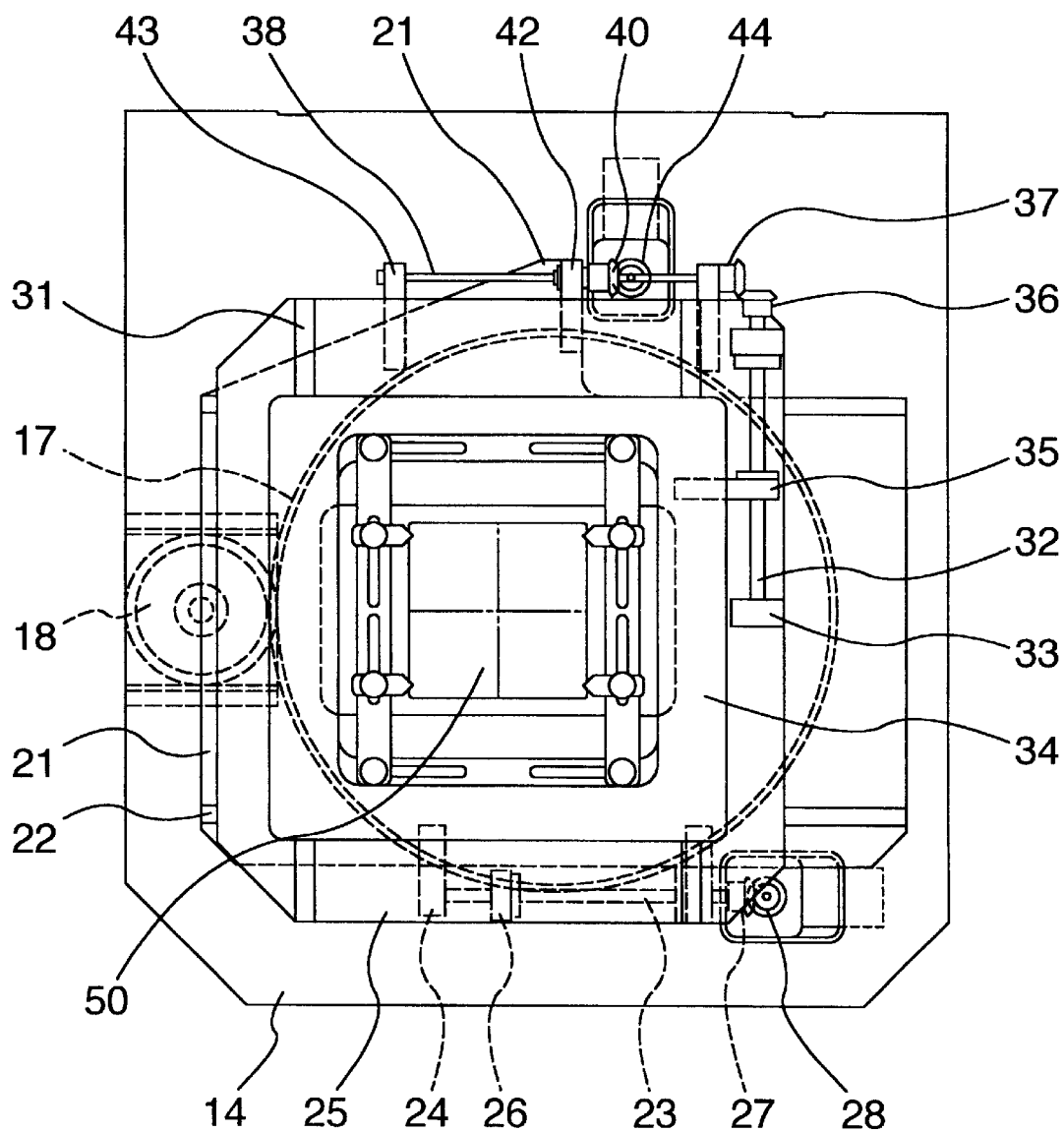
FIG. 5 is a plan view of the stage mechanism when an x-stage moves.
Figure 6:
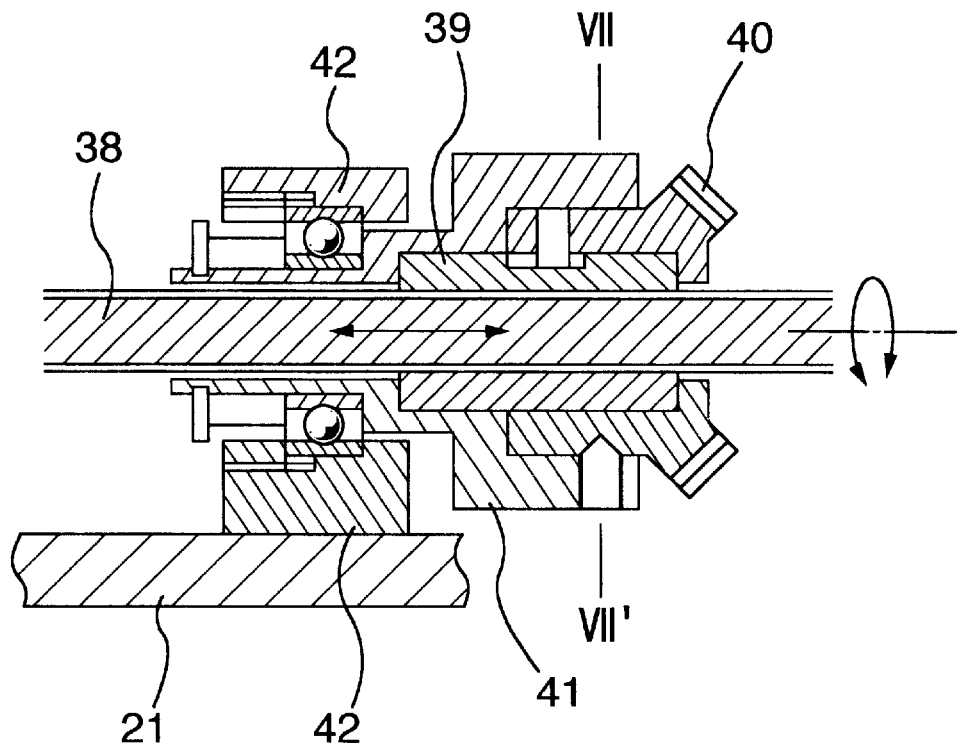
FIG. 6 is an axial, longitudinal sectional diagram of a spline nut and bevel gear portion in a y-stage moving mechanism in the embodiment of the stage mechanism.
Figure 7:
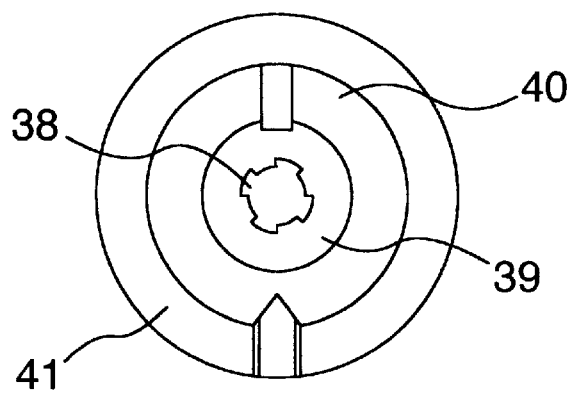
FIG. 7 is a transverse, cross-sectional diagram of the spline nut and bevel gear portion shown in FIG. 6.
Figure 8:
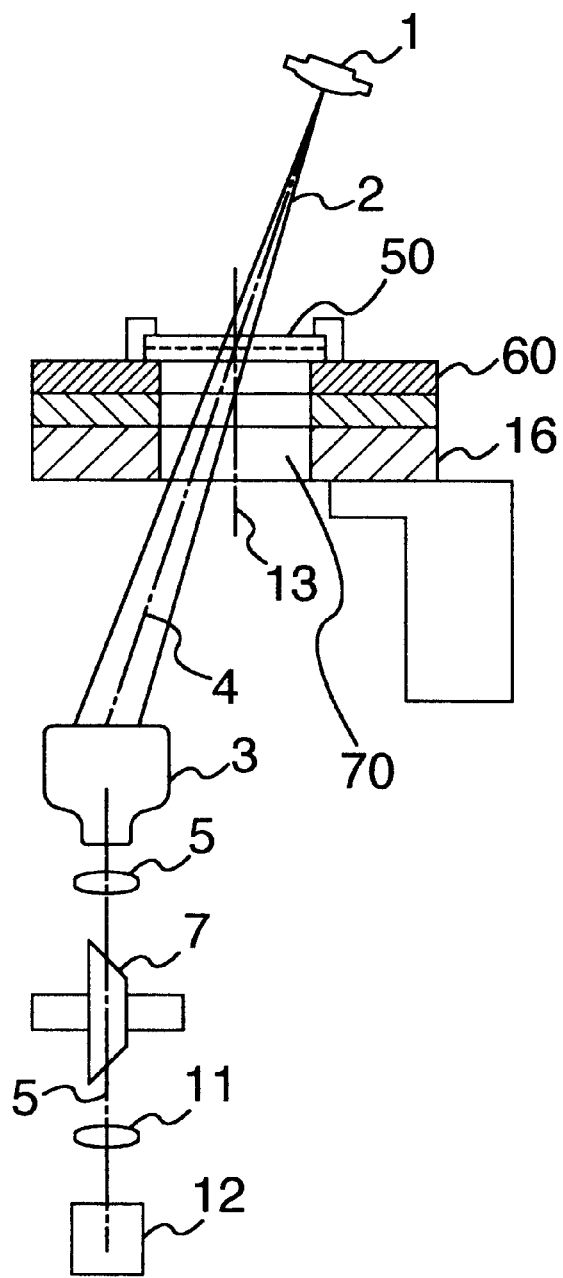
FIG. 8 is a diagram showing the construction of an X-ray laminography apparatus.

FIG. 1 shows, in partial sectional side view form, an embodiment of an X-ray laminography apparatus according to the invention, FIGS. 2 and 3 show side views of a movable stage mechanism in FIG. 1 as viewed in arrow A direction, FIGS. 4 and 5 show plan views of the movable stage mechanism in FIG. 1 as viewed in arrow B direction, FIG. 6 shows, in sectional form, details of a spline nut and bevel gear portion shown in FIGS. 4 and 5, and FIG. 7 is a cross-sectional view taken on VII–VII' in FIG. 6.

In the present specification, on the assumption that a plane on an x-stage base 21 is defined as a two-dimensional Cartesian coordinate system, "x" is defined as longitudinal direction of guides 22 and "y" is defined as longitudinal direction of guides 31 which is orthogonal to "x". An x-stage is a stage movable in the x-direction and a y-stage is a stage movable in the y-direction.

Referring to FIGS. 1 to 6, there are illustrated an X-ray source 1, an X-ray beam 2 emitted from the X-ray source, an X-ray image intensifier 3 for converting the X-ray beam into an optical image, an X-ray optical axis 4 connecting an X-ray emitting point of the X-ray source and the center of an X-ray detection surface of the X-ray image intensifier, an imaging optical system optical axis 5 passing through the X-ray detection surface center, a collimate lens 6 for forming the optical image generated by the X-ray image intensifier into a parallel light beam, an image rotating prism 7, a follower gear 8 of the image rotating prism, an image rotating prism drive gear 9, an image rotating prism drive motor 10, an image forming lens 11 for forming an image of a light beam passing through the image rotating prism on a CCD camera 12, a rotation center axis 13 of rotary stage, a rotary stage base 14, a cross-roller ring bearing 15, a hollow rotary shaft 16, a follower gear 17, a rotary stage drive gear 18, a rotary stage drive motor 19, an x-stage angular position sensor 20, the x-stage base 21, the x-stage guides 22, an x-stage drive screw 23, an x-stage drive screw bearing 24, an x-stage 25, an x-stage drive screw nut holder 26 for transmitting x-direction movement of an x-stage drive screw nut to the x-stage 25, a bevel gear 27 mounted to the x-stage drive screw 23, a bevel gear 28 which engages or meshes with the bevel gear 27 as necessary, an x-axis drive motor 29 mounted with the bevel gear 28, an air cylinder with guide 30 for forward/backward movement of the bevel gear 28 between a position for engagement with the bevel 27 and a position on the x-stage side, the y-stage guides 31, a y-stage drive screw 32, a y-stage drive screw bearing 33, a top table (y-stage) 34, a y-stage drive screw nut holder 35 for transmitting y-direction movement of the y-stage drive screw nut to the top table, a bevel gear 36 mounted to the y-stage drive screw 32, a bevel gear 37 which engages or meshes with the bevel gear 36, a spline shaft 38 mounted with the bevel gear 37 and laid in parallel with the moving direction of the x-stage, a spline nut 39 snugly fitted on the spline shaft, a bevel gear 40 coupled to the spline nut 39 coaxially thereof, a hollow sleeve 41 coupled to the bevel gear 40 concentrically thereof, a bevel gear bearing 42 connected to the x-stage base 21 to rotatably bear the hollow sleeve 41, a spline shaft bearing 43 connected to the x-stage to rotatably bear the spline shaft 38, a bevel gear 44 which engages or meshes with the bevel gear 40 as necessary, a y-stage drive motor 45 mounted with the bevel gear 44, an air cylinder with guide 46 for forward/backward movement of the bevel gear 44 between a position for engagement with the bevel gear 40 and a position on the x-stage base side, and; an object to be measured 50 which is held on the top table (y-stage) 34. In the present embodiment, the rotation center axis 13 of the rotary stage is 45° inclined with respect to the X-ray optical axis 4 and the X-ray image intensifier 3 is disposed such that its X-ray detection surface is orthogonal to the rotation center axis 13 of the x-stage 25.

Figure 10:
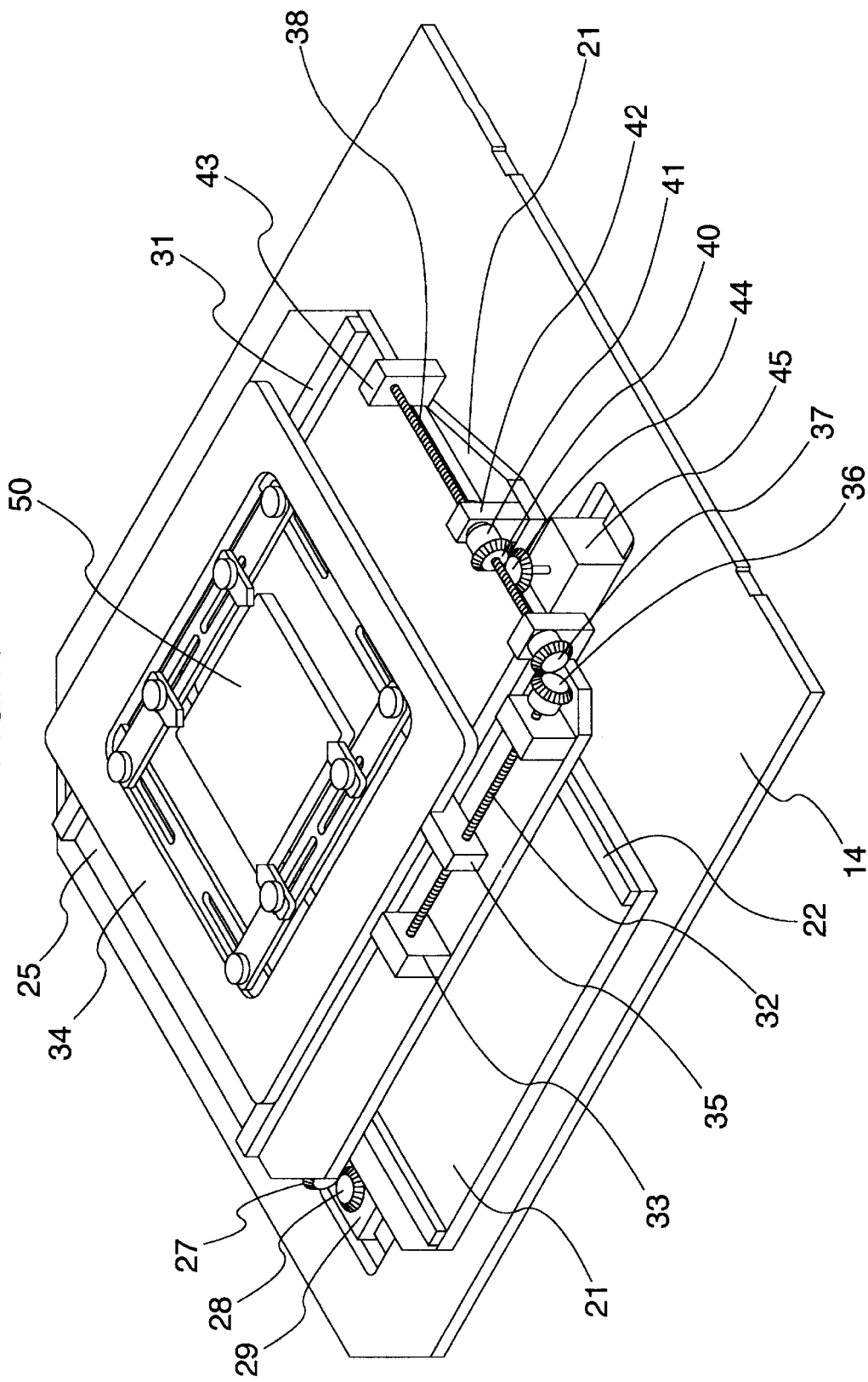
FIG. 10 is a perspective view of a movable stage portion in the X-ray tomography apparatus according to the embodiment of the invention.

FIG. 10 is a perspective view, as viewed from above, of the movable stage portion in the embodiment of the laminography apparatus according to the invention shown in FIGS. 1 to 5. The movable stage mechanism has components, enumerated herein from lower to upper, which are the stationary and unmovable base 14, the motor 19 fixed to the base 14, the hollow rotary shaft 16 driven to rotate by the motor 19, the x-stage base 21 fixed to the hollow rotary shaft 16 and rotatable along with rotation of the rotary shaft 16, the x-stage drive motor 29 fixed to the base 14, the guides 22 fixed on the x-stage base 21, the x-stage 25 slidable along the guides 22, the y-stage drive motor 45 fixed to the base 14, the guides 31 fixed on the x-stage 25, and the y-stage (top table) 34 slidable along the guides 31. The object 50 to be photographed is fixed to the y-stage 34 by means of a chuck. When positioning a photography position of the target object 50, the movable stage mechanism is operated as below. During rotation of the x-stage 25, the angular position sensor 20 detects, on the basis of a rotation angle of the x-stage 25, that the bevel gear 27 of the x-stage drive screw reaches a position where the bevel gear 27 is engageable with the bevel gear 28 of the x-stage drive motor 29. Then, the rotation of the x-stage 25 stops at the predetermined angular position. As the air cylinder 30 ascends, the bevel gear 28 mounted to the rotary shaft of the x-stage drive motor 29 engages or meshes with the bevel gear 27 of the x-stage drive screw to drive the x-stage drive screw and as the air cylinder 46 ascends, the bevel gear 44 connected to the rotary shaft of the y-stage drive motor 45 engages or meshes with the bevel gear 40 connected to the y-stage drive screw to drive the y-stage drive screw. Since the bevel gear 40 is mounted to the spline shaft 38 and is therefore always held at the same position regardless of the movement of the x-stage 25, rotating of the y-stage drive motor 45 can be transmitted to the bevel gear 40.

To describe more specifically with reference to FIG. 6, the hollow sleeve 41 rotates along with the rotation of the bevel gear 40 to rotate the spline shaft 38. On the other hand, the bearing 42 is fixed on the x-stage base 21 to rotatably support the sleeve 41. The spline shaft 38 is rotatably supported on the x-stage 25 through the medium of the bearing 43, so that the spline shaft now rotating about the sleeve 41, unmovable in the x-axis direction, to move the y-stage 34 slides in its axial direction as the x-stage 25 moves. Through this, during a stoppage of rotation of the x-stage base 21, the x-stage 25 and the y-stage (top table) 34 can be moved independently so as to position a desired observation area while irradiating the X-ray beam to the object 50 and observing a transmission image of the object 50 on a monitor. Since both the x-stage drive motor 29 and the y-stage drive motor 45 are arranged on the stationary and unmovable base 14, electric power can be supplied continuously to the motors very easily without resort to any slip rings and brushes.

On the other hand, when the positioning of the observation position for the object 50 ends and operation of taking tomograms starts, the movable stage mechanism operates as follows. The air cylinders 30 and 46 are inactivated to release the engagement of bevel gear 28 with bevel gear 27 and the engagement of bevel gear 44 with bevel bear 40, thereby stopping the x-stage 25 and the y-stage (top stage) 34. Then, the motor 19 is rotated to rotate the x-stage base 21 a predetermined speed, and the X-ray beam transmitting through the object 50 is detected on the detection surface 3 so as to produce a tomographic image.

Figure 9:
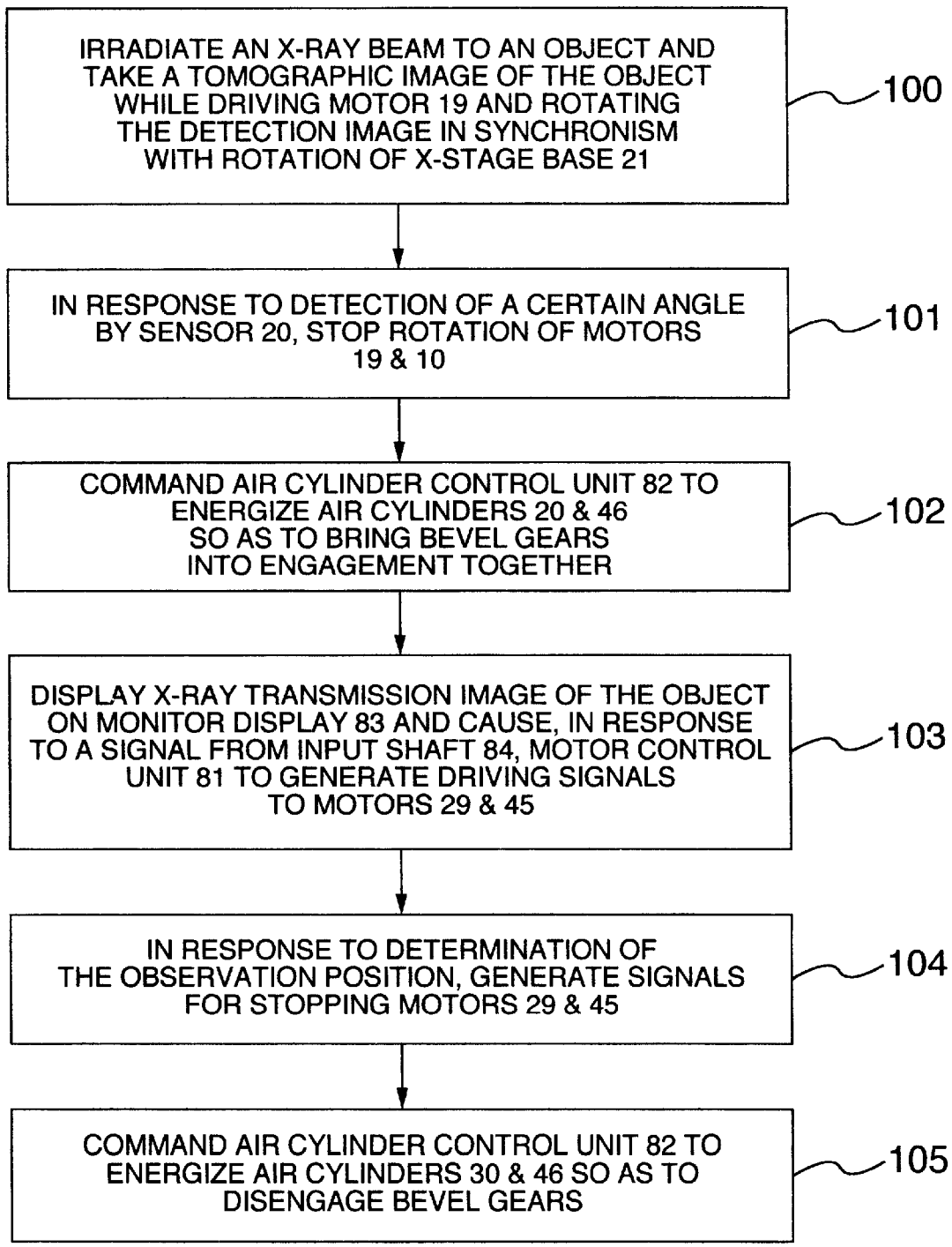
FIG. 9 is a flow chart showing the procedure ranging over operation for positioning of a tomography site and operation for taking tomograms.

Referring now to an embodiment of a control system shown in FIG. 1 and a flow chart of FIG. 9, tomographic operation and positioning operation will be further described. The control system has a computer 80, a motor control unit 81 responsive to signals from the computer 80 to drive or stop the motor 10, 19, 29 and 45, an air cylinder control unit 82 responsive to signals from the computer 80 to cause the air cylinders 30 and 46 to ascend or descend, a monitor display 83 for displaying an X-ray transmission image or a tomographic image of the object 50 which is obtained by image-processing an output signal from the CCD camera 12 with the computer 80, and an input unit 84 for designating stop positions of the x stage 25 and y stage 34. The computer 80 may be a known microcomputer having a CPU (not shown) and a memory unit (not shown) for storing a control program for execution of operation of the flow chart shown in FIG. 9 and a known image processing program.

In step 100, with the X-ray beam 2 emitted from the X-ray source 1 to the top table 34 and the motor 19 rotated under the control of the computer 80, an X-ray image is detected and converted into an optical image by means of the X-ray image intensifier 3. The optical image is passed through the collimate lens 6, image rotating prism 7 and image forming lens 11 and picked up by the CCD camera 12 to provide an X-ray image which in turn is rotated in synchronism with rotation of the object 50 by the rotation of the x-stage base 21. The rotation speed is 1 to 5 revolutions/sec. While irradiating the X-ray beam 2 to the object 50 rotating about the rotary axis 13 inclined with respect to the X-ray optical axis 4, an X-ray image is detected on a detection plane orthogonal to the rotation center axis 13 and the detected image is rotated in synchronism with the rotation of the object, thereby obtaining a tomographic image on a plane orthogonal to the rotation center axis 13 and including an intersection of the X-ray optical axis 4 and the rotation center axis 13.

When observation of a measuring area of the object ends and observation of a different area is then desired, the motor 19 is controlled on the basis of the rotation angle detected by the angular position sensor 20 of the rotary stage under the control of the computer 80 while irradiating the X-ray beam to stop the x-stage base 21 at a rotation angle where the bevel gear 27 engages the bevel gear 28 and the bevel gear 40 engages the bevel gear 44 and at the same time, the image rotating prism drive motor 10 is also stopped (step 101).

Under the stop condition of the measured object 50 and image rotating prism 7, an overall projection image of an X-ray beam transmitting portion of the measured object 50 can be obtained in a direction of thickness of the portion, the next observation point can be determined by watching the transmitting X-ray image on the monitor 83. In step 102, the air cylinders with guide 30 and 46 are operated under the control of the computer 80 to advance the bevel gears 28 and 44 so as to bring the bevel gear 28 into engagement with the bevel gear 27 and bring the bevel gear 44 into engagement with the bevel gear 40.

Subsequently, in step 103, while watching the X-ray transmission image of the object 50 displayed on the screen of the monitor display 83, the operator manipulates the input unit 84 to designate movement of the x-stage 25 and y-stage 34 for the sake of seeking a position for tomographic operation. The input unit 84 may be of the type of either generating a signal for commanding movement of the stages only during continuation of depression of a button by the operator, inputting moving distances in the x-and y-directions or inputting coordinate positions of movement destinations of the x- and y-stages. In any case, the computer 80 responds to an output signal from the input unit 84 to supply to the motor control unit 81 commands for controlling the x-stage drive motor 29 and y-stage drive motor 45. For example, only the x-stage 25 is moved from the position shown in FIG. 4 to the position shown in FIG. 5 to determine a position where a tomogram is to be taken, the program proceeds to step 104 in which the x-stage 25 is stopped. Subsequently, in step 105, the air cylinders with guide 30 and 46 are operated under the control of the computer 80 to retreat the bevel gears 28 and 44 in order that these gears are drawn back as shown in FIG. 3 to positions where they do not interfere with the rotary body such as the x-stage base 21.

Thereafter, the program returns to the step 100 and the x-stage drive motor 19 and the rotating prism drive motor 10 are again driven, thereby ensuring that a tomographic image of a desired portion of the object 50 can be obtained.

In case the observation tomographic plane is desired to be changed in the direction of the thickness of the object (z-direction vertical to the xy-plane), the whole of the x-stage base 21 and x-and y-stages 25 and 34 is moved in a direction parallel to the rotation center axis 13 of the x-stage base 21 to move the object 50 in the z-direction, causing a plane including an intersection of the center axis 13 of the x-stage base 21 and the X-ray optical axis 4 to move relative to the thickness direction of the object and tomographic plane to be observed can be changed.

As described above, according to the present invention, since the position to be measured can be determined while irradiating the X-ray beam and observing a transmission image to permit immediate observation of a tomographic image at the desired area, an inner layer of a multilayer printed board and internal defects of electronic parts and mechanical parts can be found easily and an inspection apparatus making full use of the function of the laminography apparatus can be constructed.

Besides, since any slip ring rotatable at a high speed and brush electrode are not used, a compact, highly-reliable and inexpensive apparatus can be provided.

What is claimed is:

1. An X-ray tomography apparatus for taking tomograms inside an object, comprising:

an X-ray source for irradiating an X-ray beam to said object;

an X-ray detection unit for detecting said X-ray beam transmitting through said object to generate a transmission image of said object on the basis of the detected X-ray beam;

an XY-stage, on which said object is placed;

a display unit for monitoring said transmission image of said object;

a moving mechanism coupled with said XY-stage and a drive unit for moving said object to change an X-ray irradiation area of said object;

a control unit for controlling said moving mechanism to stop said object at a desired position in accordance with the transmission image monitored by said display unit, and disconnecting said moving mechanism of said XY-stage from said drive unit; and a rotating mechanism for rotating said object about a rotation axis inclined by a predetermined angle with respect to an irradiation axis of said X-ray beam;

wherein said X-ray detection unit detects said X-ray beam transmitting through said object and rotates the detected image in synchronism with the rotation of said object to provide a rotation image, an image of tomogram of said object including an intersection of said rotation axis and said irradiation axis;

said drive unit comprising first drive unit for driving said moving mechanism;

a second drive unit for driving said rotating mechanism;

a first coupling mechanism for coupling said moving mechanism to said first drive unit;

a second coupling mechanism for coupling said rotating mechanism to said second drive unit; and a sensor unit for detecting a rotation position of said rotating mechanism, wherein when said sensor unit detects a predetermined rotation position while said rotating mechanism is rotating, said control unit controls said second coupling mechanism so as to disconnect said rotating mechanism from said second drive unit and further controls said first coupling mechanism so as to couple said moving mechanism to said first drive unit; and a base for fixing said first and second drive units, said base being arranged independently of movement of said moving mechanism and rotating mechanism.

2. A method of taking tomograms inside an object with an X-ray tomography apparatus, comprising the steps of:

irradiating an X-ray beam to said object on an xy-stage;

detecting said X-ray beam transmitting through said object and generating a transmission image of said object on the basis of the detected X-ray beam;

monitoring said transmission image of said object on a display;

moving said object by means of a moving mechanism of said xy-stage coupled to a drive unit to change an X-ray irradiation said object;

stopping said object at a desired position in accordance with said transmission image monitored on said display;

disconnecting said moving mechanism of said XY-stage from said drive unit;

rotating said object, irradiated with the X-ray beam about a rotation axis inclined with respect to an irradiation axis of the X-ray beam, by means of a rotating mechanism; and detecting an X-ray beam transmitting through said object and rotating a detected image in synchronism with the rotation of said object to provide a rotation image and generating, on the basis of the rotation image, an image of a tomogram of said object including an intersection of said rotation axis and said irradiation axis; and coupling of said moving mechanism to said drive unit when said rotating mechanism is at a predetermined rotation position.

3. A method of taking tomograms inside an object with an X-ray tomography apparatus, comprising the steps of:

irradiating an X-ray beam to said object on an xy-stage;

detecting said X-ray beam transmitting through said object and generating a transmission image of said object on the basis of the detected X-ray beam;

monitoring said transmission image of said object on a display;

moving said object by means of a moving mechanism of said xy-stage coupled to a drive unit to change an X-ray irradiation said object;

stopping said object at a desired position in accordance with said transmission image monitored on said display;

disconnecting said moving mechanism of said XY-stage from said drive unit;

rotating said object, irradiated with the X-ray beam about a rotation axis inclined with respect to an irradiation axis of the X-ray beam, by means of a rotating mechanism; and detecting an X-ray beam transmitting through said object and rotating a detected image in synchronism with the rotation of said object to provide a rotation image and generating, on the basis of the rotation image, an image of a tomogram of said object including an intersection of said rotation axis and said irradiation axis;

detecting the rotation position of said rotating mechanism during rotation of said rotating mechanism, and stopping the rotation and coupling said moving mechanism to said drive unit when the detected rotation position coincides with the predetermined position.

4. An X-ray tomography apparatus for taking tomograms inside an object, comprising:

an X-ray source for irradiating an X-ray beam to the object;

a stationary base;

first, second and third motors fixed to said stationary base;

a hollow shaft driven to rotate by said first motor and having an opening in the center of rotation;

an x-stage base fixed to said hollow shaft;

x-guide rails fixed on said x-stage base;

an x-stage slidable on said guide rails;

y-guide rails fixed on said x-stage;

a y-stage slidable on said y-guide rails, said object being detachably mounted on said y-stage;

an angular position sensor for detecting a rotation position of said x-stage base;

a first bevel gear mounted to a rotary shaft of said second motor;

an x-stage drive unit having a second bevel gear and driven by rotation of said second bevel gear to move said x-stage on said x-guide rails, said x-stage drive unit being supported by said x-stage;

a third bevel gear mounted to a rotary shaft of said third motor;

a y-stage drive unit having a fourth bevel gear and driven by rotation of said fourth bevel gear to move said y-stage on said y guide rails, said y-stage drive unit being supported on said x-stage and said fourth bevel gear being always held at a fixed position on said x-stage regardless of movement of said x-stage;

a first actuator for moving said first bevel gear to bring it into engagement with said second bevel gear;

a second actuator for moving said third bevel gear to bring it into engagement with said fourth gear;

a control unit responding to detection of a predetermined rotation angle by said angular position sensor to stop the rotation of said first motor and control said first and second actuators so as to release engagement of said first bevel gear with said second bevel gear and bring said third bevel gear into engagement with said fourth bevel gear; and an X-ray detection unit having a detection portion for detecting an X-ray beam transmitting through said object and passing through said opening to provide an image, rotating the detection image in synchronism with the rotation of said object to provide a rotation image and generating a tomographic image of said object on the basis of the rotation image.

5. An X-ray tomography apparatus according to claim 4, wherein said y-stage drive unit includes:

a spline shaft having a rotation axis parallel to the moving direction of said x-stage;

a spline nut operatively coupled to said fourth bevel gear and said spline shaft with sharing a common rotation axis for transmitting rotation of said fourth bevel gear to said spline shaft and freely movable along an axis of said spline shaft;

a first bearing member fixed to said x-stage base for supporting said spline shaft to be rotatable via said spline nut at a fixed position above said x-stage base;

a second bearing member fixed to said x-stage and operative to rotatably support said spline shaft;

a y-stage drive screw receiving rotation transmitted from said spline shaft and having a rotation axis parallel to the moving direction of said y-stage;

a third bearing member fixed to said y-stage and responding to the rotation of said spline shaft to move said y-stage; and a fourth bearing member fixed to said x-stage and rotatably supporting said spline shaft.

6. An X-ray tomography apparatus for taking tomograms inside an object, comprising:

an X-ray source for irradiating an X-ray beam to said object;

an X-ray detection unit for detecting said X-ray beam transmitting through said object to generate a transmission image of said object on the basis of the detected X-ray beam;

an XY-stage, on which said object is placed;

a display unit for monitoring said transmission image of said object;

a moving mechanism coupled with said XY-stage and a drive unit for moving said object to change an X-ray irradiation area of said object;

a control unit for controlling said moving mechanism to stop said object at a desired position in accordance with the transmission image monitored by said display unit, and disconnecting said moving mechanism of said XY-stage from said drive unit; and a rotating mechanism for rotating said object about a rotation axis inclined by a predetermined angle with respect to an irradiation axis of said X-ray beam;

wherein said X-ray detection unit detects said X-ray beam transmitting through said object and rotates the detected image in synchronism with the rotation of said object to provide a rotation image, an image of tomogram of said object including an intersection of said rotation axis and said irradiation axis;

said drive unit comprising first drive unit for driving said moving mechanism;

a second drive unit for driving said rotating mechanism;

a first coupling mechanism for coupling said moving mechanism to said first drive unit;

a second coupling mechanism for coupling said rotating mechanism to said second drive unit; and a sensor unit for detecting a rotation position of said rotating mechanism, wherein when said sensor unit detects a predetermined rotation position while said rotating mechanism is rotating, said control unit controls said second coupling mechanism so as to disconnect said rotating mechanism from said second drive unit and further controls said first coupling mechanism so as to couple said moving mechanism to said first drive unit.

* * * * *